United States Patent [19]
Barlet

[11] Patent Number: 5,906,216
[45] Date of Patent: May 25, 1999

[54] DENTURE CLEANING DEVICE

[76] Inventor: Bruce N. Barlet, 483 Locust St., Mertztown, Pa. 19539

[21] Appl. No.: 08/947,515

[22] Filed: Oct. 10, 1997

[51] Int. Cl.[6] ........................................................ B08B 3/04
[52] U.S. Cl. ........................ 134/58 R; 134/184; 134/135; 134/901
[58] Field of Search ..................................... 134/184, 187, 134/188, 135, 901, 58 R, 140

[56] References Cited

U.S. PATENT DOCUMENTS

| | | | |
|---|---|---|---|
| 3,132,657 | 5/1964 | Ciccone | 134/188 |
| 3,151,846 | 10/1964 | George | 134/184 |
| 3,265,369 | 8/1966 | Harrison | 134/188 |
| 3,406,696 | 10/1968 | MacChesney et al. | 134/58 R |
| 3,421,528 | 1/1969 | Gomez et al. | 134/188 |
| 4,157,922 | 6/1979 | Luik | 134/58 R |
| 4,732,187 | 3/1988 | Monch | 134/135 |
| 4,922,939 | 5/1990 | Adamczyk | 134/140 |
| 5,237,778 | 8/1993 | Baer | 51/163.1 |

Primary Examiner—Frankie L. Stinson
Assistant Examiner—Paul J. Lee

[57] ABSTRACT

A denture cleaning apparatus is provided including a housing including a lower extent and an upper extent. A basket is situated in the upper extent of the housing. An agitator is rotatably mounted within the upper extent of the housing below the basket. Finally, a motor is mounted within the lower extent of the housing and coupled to the agitator for rotating the same only during the receipt of power.

5 Claims, 2 Drawing Sheets

DENTURE CLEANING DEVICE

BACKGROUND OF THE INVENTION

1. Field of the Invention

The present invention relates to denture cleaners and more particularly pertains to a new denture cleaning device for cleaning soiled dentures with agitated fluid.

2. Description of the Prior Art

The use of denture cleaners is known in the prior art. More specifically, denture cleaners heretofore devised and utilized are known to consist basically of familiar, expected and obvious structural configurations, notwithstanding the myriad of designs encompassed by the crowded prior art which have been developed for the fulfillment of countless objectives and requirements.

Known prior art denture cleaners include U.S. Pat. No. 4,336,816; U.S. Pat. No. 5,275,185; U.S. Pat. No. 4,891,857; U.S. Pat. No. 4,922,939; and U.S. Pat. Des. No. 261,423.

In these respects, the denture cleaning device according to the present invention substantially departs from the conventional concepts and designs of the prior art, and in so doing provides an apparatus primarily developed for the purpose of cleaning soiled dentures with agitated fluid.

SUMMARY OF THE INVENTION

In view of the foregoing disadvantages inherent in the known types of denture cleaners now present in the prior art, the present invention provides a new denture cleaning device construction wherein the same can be utilized for cleaning soiled dentures with agitated fluid.

The general purpose of the present invention, which will be described subsequently in greater detail, is to provide a new denture cleaning device apparatus and method which has many of the advantages of the denture cleaners mentioned heretofore and many novel features that result in a new denture cleaning device which is not anticipated, rendered obvious, suggested, or even implied by any of the prior art denture cleaners, either alone or in any combination thereof.

To attain this, the present invention generally comprises a housing with a lower extent having a cylindrical configuration. The lower extent has a first diameter and a first height. It is further defined by a circular top face, a circular bottom face, and a periphery formed therebetween thus defining an interior space. The housing also includes an upper extent with a second diameter less than the first diameter and a second height greater than the first height. As best shown in FIG. 3, the upper extent has a circular top opening, a circular bottom face integrally coupled to the top face of the lower extent in concentric relationship therewith, and a periphery formed therebetween thus defining an interior space. For reasons that will become apparent hereinafter, the upper extent has a pair of diametrically opposed tangs integrally coupled to the periphery within the interior space and adjacent to the top opening of the upper extent. For precluding movement thereof on a recipient surface, a plurality of elastomeric pads are mounted to the bottom face of the lower extent of the housing. Next provided is a cover having a disk-shaped configuration. For handling purposes, a cylinder is mounted along a diameter of a top face of the cover. The cover further has an annular detent with a diameter less than that of the cover. Such detent extends radially outwardly for removably engaging an annular indent formed in the periphery of the upper extent of the housing. A gasket is mounted to the bottom face of the cover adjacent to a periphery thereof. In such orientation, the gasket is adapted for engaging a top peripheral edge of the housing when the cover is mounted over the top opening of the housing. FIG. 3 shows a basket having an upper ring with two semi-circular basket portions coupled thereto and depending downwardly therefrom. Each basket is formed of a semi-circular bottom face with a periphery defined by an arcuate extent and a planar extent. It should be noted that each basket is constructed from a plurality of meshed wires. The planar extents of the baskets are spaced to define a slot. As such, the basket may be removably situated within the interior space of the upper extent of the housing, whereby the upper ring rests on the tangs of the housing such that they reside in the slot of basket. With reference still to FIG. 3, a blade assembly is shown including an agitator rotatably mounted within the interior space of the upper extent of the housing. Such agitator is positioned below the basket adjacent the bottom face of the housing. A motor is mounted within the interior space of the lower extent of the housing and is further coupled to the agitator for rotating the same only during the receipt of power. Finally, a timer mechanism is positioned on the periphery of the lower extent of the housing. The timer mechanism is connected between the blade assembly and a power source. The timer mechanism is adapted to intermittently supply the blade assembly with power in one-minute intervals for a predetermined user-selected amount of time.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new denture cleaning device apparatus and method which has many of the advantages of the denture cleaners mentioned heretofore and many novel features that result in a new denture cleaning device which is not anticipated, rendered obvious, suggested, or even implied by any of the prior art denture cleaners, either alone or in any combination thereof.

It is another object of the present invention to provide a new denture cleaning device which may be easily and efficiently manufactured and marketed.

It is a further object of the present invention to provide a new denture cleaning device which is of a durable and reliable construction.

An even further object of the present invention is to provide a new denture cleaning device which is susceptible of a low cost of manufacture with regard to both materials and labor, and which accordingly is then susceptible of low prices of sale to the consuming public, thereby making such denture cleaning device economically available to the buying public.

Still yet another object of the present invention is to provide a new denture cleaning device which provides in the apparatuses and methods of the prior art some of the advantages thereof, while simultaneously overcoming some of the disadvantages normally associated therewith.

Still another object of the present invention is to provide a new denture cleaning device for cleaning soiled dentures with agitated fluid.

Even still another object of the present invention is to provide a new denture cleaning device that includes a housing including a lower extent and an upper extent. A basket is situated in the upper extent of the housing. An agitator is rotatably mounted within the upper extent of the housing below the basket. Finally, a motor is mounted within the lower extent of the housing and coupled to the agitator for rotating the same only during the receipt of power.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
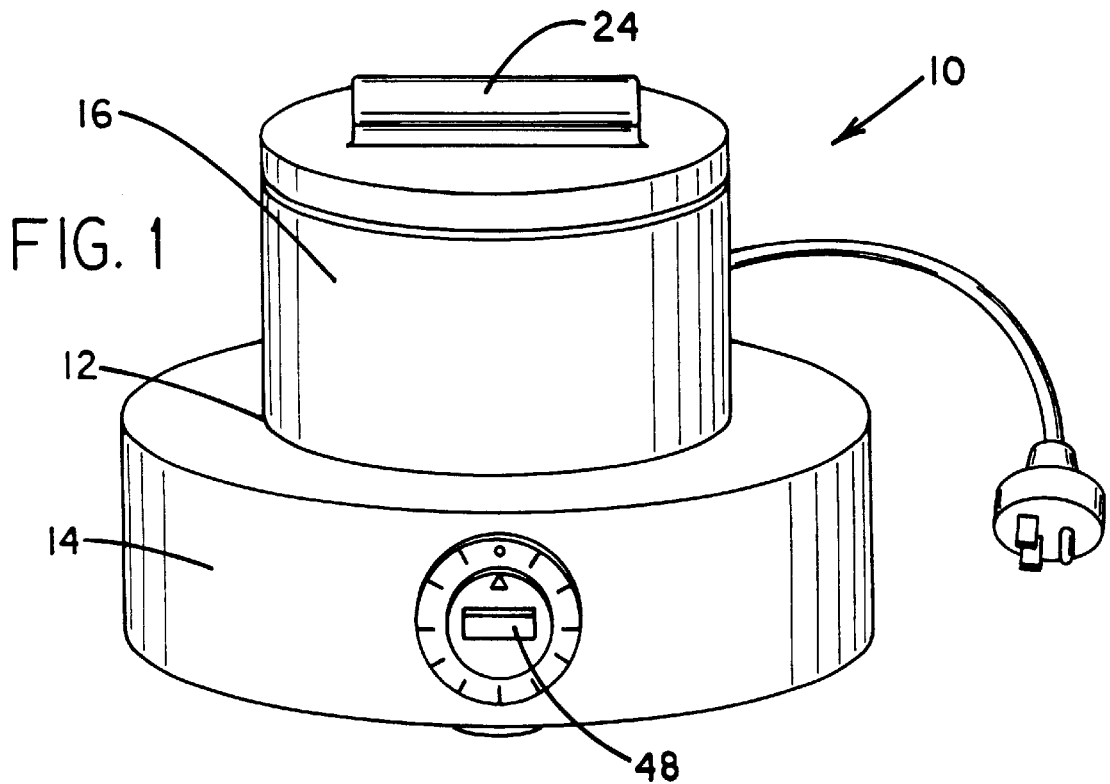
FIG. 1 is a front perspective view of a new denture cleaning device according to the present invention.
Figure 2:
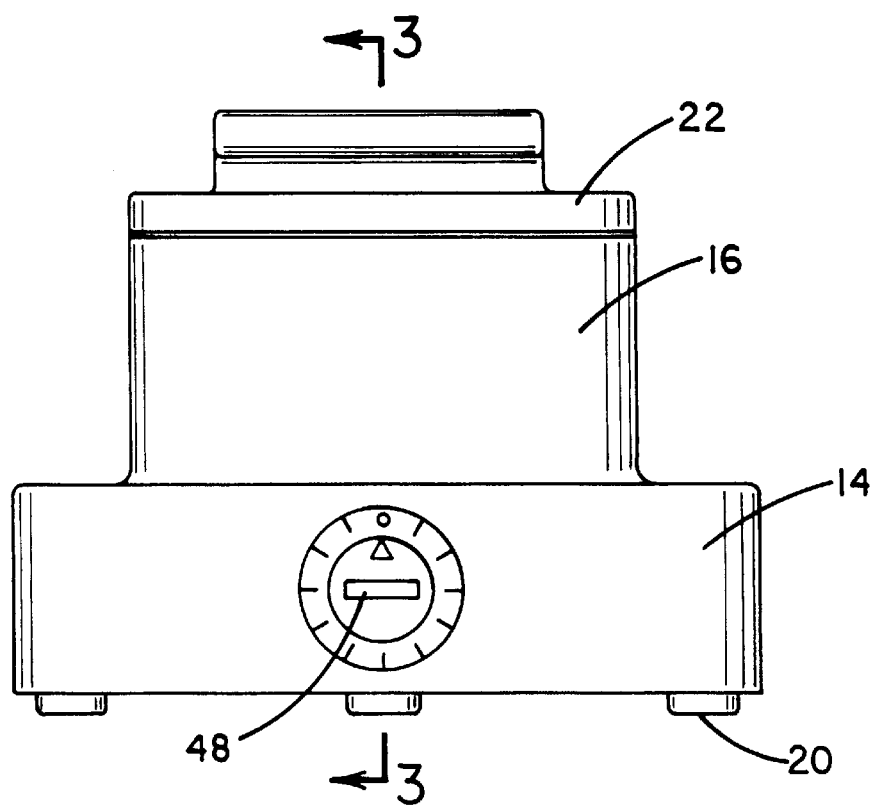
FIG. 2 is a front view of the present invention.

With reference now to the drawings, and in particular to FIGS. 1 through 4 thereof, a new denture cleaning device embodying the principles and concepts of the present invention and generally designated by the reference numeral 10 will be described.

Figure 3:
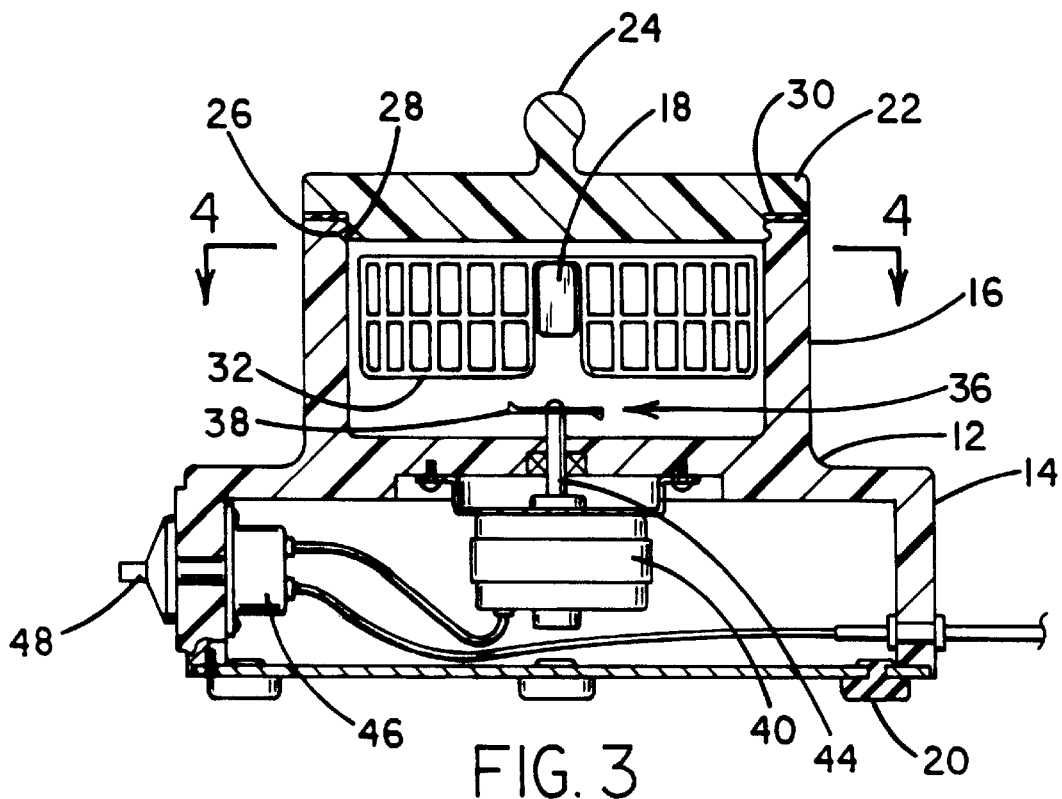
FIG. 3 is a cross-sectional view of the present invention taken along line 3—3 shown in FIG. 2.
Figure 4:
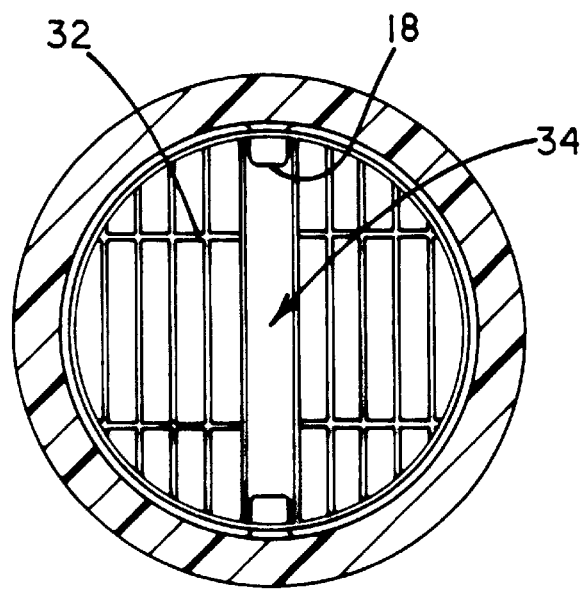
FIG. 4 is a top view of the present invention with the cover removed.

The present invention, as designated as numeral 10, includes a housing 12 with a lower extent 14 having a cylindrical configuration. The lower extent has a first diameter and a first height. It is further defined by a circular top face, a circular bottom face, and a periphery formed therebetween thus defining an interior space. The housing also includes an upper extent 16 with a second diameter less than the first diameter and a second height greater than the first height. As best shown in FIG. 3, the upper extent has a circular top opening, a circular bottom face integrally coupled to the top face of the lower extent in concentric relationship therewith, and a periphery formed therebetween thus defining an interior space. In the alternative, the upper extent may be removably coupled to the lower extent.

For reasons that will become apparent hereinafter, the upper extent has a pair of diametrically opposed block-shaped tangs 18 integrally coupled to the periphery within the interior space and adjacent to the top opening of the upper extent. To preclude movement of the housing on a recipient surface, a plurality of elastomeric pads 20 are mounted to the bottom face of the lower extent of the housing.

Next provided is a cover 22 having a disk-shaped configuration. For handling purposes, a cylinder 24 is mounted along a diameter of a top face of the cover. A bottom face of the cover further has an annular detent 26 with a diameter less than that of the cover. Such detent extends radially outwardly for removably and snappily engaging an annular indent 28 formed in the periphery of the upper extent of the housing. A gasket 30 is mounted to the bottom face of the cover adjacent to a periphery thereof. In such orientation, the gasket is adapted for engaging a top peripheral edge of the housing when the cover is mounted over the top opening of the housing.

FIG. 3 shows a basket 32 having an upper ring with two semi-circular basket portions coupled thereto and depending downwardly therefrom. Preferably, the basket has a height of about ¾ the height of the upper extent of the housing. Each basket portion is formed of a semi-circular bottom face with a periphery defined by an arcuate extent and a planar extent. It should be noted that each basket is constructed from a plurality of meshed wires. The planar extents of the basket portions are spaced to define a slot 34. As such, the basket may be removably situated within the interior space of the upper extent of the housing, whereby the upper ring rests on the tangs of the such that it resides in the slot of basket.

With reference still to FIG. 3, a blade assembly is shown including an agitator 36 rotatably mounted within the interior space of the upper extent of the housing. Such agitator is positioned below the basket adjacent the bottom face of the housing. In the preferred embodiment, the agitator includes a pair of dull blades each angled above and below the horizontal by about 1 degree, respectively. Further, each blade ideally has an upturned end 38. The specific design of the blade is tailored for producing sonic waves upon the rotation thereof in a liquid medium.

A motor 40 is mounted within the interior space of the lower extent of the housing and is further coupled to the agitator for rotating the same only during the receipt of power. The motor is ideally coupled to the agitator by way of a post 44 which extends through the top face of the lower extent and the bottom face of the upper extent of the housing.

Finally, a timer mechanism 46 is positioned on the periphery of the lower extent of the housing. The timer mechanism is connected between the blade assembly and a power source. As an option, a portable power source may be employed which is positioned in the lower extent of the housing. The timer mechanism is adapted to intermittently supply the blade assembly with power in one-minute intervals for a predetermined user-selected amount of time. A user may select such amount of time by way of a dial 48 mounted on the housing. In the preferred embodiment, the timer is set to 5-minutes to provide adequate time for cleaning dentures situated within the basket.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A denture cleaning apparatus comprising, in combination:

a housing including a lower extent with a cylindrical configuration having a first diameter and a first height, the lower extent being defined by a circular top face, a circular bottom face, and a periphery formed therebetween thus defining an interior space, the housing further including an upper extent with a second diameter less than the first diameter and a second height greater than the first height, the upper extent being defined by a circular top opening, a circular bottom face integrally coupled to the top face of the lower extent in concentric relationship therewith, and a periphery formed therebetween thus defining an interior space, the upper extent having a pair of diametrically opposed block-shaped tangs integrally coupled to the periphery within the interior space and adjacent to the top opening of the upper extent;

a plurality of elastomeric pads mounted to the bottom face of the lower extent of the housing for precluding movement thereof on a recipient surface;

a cover having a disk-shaped configuration with a cylinder mounted along a diameter of a top face of the cover for handling purposes, the cover further having an annular detent with a diameter less than that of the cover and extending radially outwardly for removably engaging an annular indent formed in an interior surface of the periphery of the upper extent of the housing to secure the cover to the housing when a liquid is agitated in the upper extent, wherein a gasket is mounted to the bottom face of the cover adjacent to a periphery thereof for engaging a top peripheral edge of the housing when the cover is mounted over the top opening of the housing;

a basket with a height ¾ that of the upper extent of the housing and having an upper ring with two semi-circular basket portions each adapted to hold a denture plate the semi-circular basket portions being coupled to the upper ring and depending downwardly therefrom each formed of a semi-circular bottom face with a periphery defined by an arcuate extent and a planar extent, each basket constructed from a plurality of meshed wires, wherein the planar extents of the baskets are spaced to define a slot such that the basket may be removably situated within the interior space of the upper extent of the housing wherein the upper ring rests on the tangs of the housing with the tangs residing in the slot of basket, the basket being spaced above the circular bottom face of the housing when the upper ring engages the tangs to position dentures in the basket from any debris on the bottom face;

a blade assembly including an agitator rotatably mounted within the interior space of the upper extent of the housing in a position adjacent to and above the bottom face thereof and a motor mounted within the interior space of the lower extent of the housing and coupled to the agitator for rotating the same only during the receipt of power, the agitator being positioned below the semi-circular bottom faces of the basket, the blade assembly including a pair of blades angled upwardly and downwardly, respectively, by about 1 degree with respect to a horizontal for producing sonic waves upon the rotation thereof in a liquid medium; and a timer mechanism positioned on the periphery of the lower extent of the housing and connected between the blade assembly and a power source, the timer mechanism adapted to intermittently supply the blade assembly with power in one-minute intervals for a predetermined user-selected amount of time.

2. A denture cleaning apparatus comprising:

a housing including a lower extent and an upper extent, the upper extent being defined by a circular top opening, a circular bottom face integrally coupled to a top face of the lower extent in concentric relationship therewith, and a periphery formed therebetween thus defining an interior space, the upper extent having a pair of diametrically opposed tangs integrally coupled to the periphery within the interior space and adjacent to the top opening of the upper extent;

a basket having an upper ring with two semi-circular basket portions coupled thereto and depending downwardly therefrom each formed of a semi-circular bottom face with a periphery defined by an arcuate extent and a planar extent, each basket constructed from a plurality of meshed wires, wherein the planar extents of the baskets are spaced to define a slot such that the basket may be removably situated within the interior space of the upper extent of the housing wherein the upper ring rests on the tangs of the housing with the tangs residing in the slot of basket;

an agitator mounted within the housing adjacent the basket and a motor coupled to the agitator for actuating the same only during the receipt of power, the agitator including a pair of blades angled upwardly and downwardly, respectively, with respect to a horizontal for producing sonic waves upon the rotation thereof in a liquid medium; and a timer adapted to intermittently supply the agitator with power in intervals for a predetermined user-selected amount of time.

3. A denture cleaning apparatus as set forth in claim 2 and further including a plurality of elastomeric pads mounted to a bottom face of the housing for precluding movement thereof on a recipient surface.

4. A denture cleaning apparatus as set forth in claim 2 and further including a cover being releasably mounted on the housing.

5. A denture cleaning apparatus as set forth in claim 2 and further including a cover having a disk-shaped configuration with a handle mounted thereon, the cover further having an annular detent with a diameter less than that of the cover and extending radially outwardly for removably engaging an annular indent formed in an interior surface of the periphery of the upper extent of the housing to secure the cover to the housing, wherein a gasket is mounted to the bottom face of the cover adjacent to a periphery thereof for engaging a top peripheral edge of the housing when the cover is mounted over the top opening of the housing.

* * * * *